US008695418B2

(12) United States Patent
Sparks et al.

(10) Patent No.: US 8,695,418 B2
(45) Date of Patent: *Apr. 15, 2014

(54) FLUIDIC SYSTEMS AND METHODS OF DETERMINING PROPERTIES OF FLUIDS FLOWING THEREIN

(75) Inventors: Douglas Ray Sparks, Whitmore Lake, MI (US); Michael W. Putty, Grosse Point Woods, MI (US); Nader Najafi, Ann Arbor, MI (US); Richard Thayre Smith, Saline, MI (US)

(73) Assignee: Integrated Sensing Systems, Inc., Ypsilanti, MI (US)

( * ) Notice: Subject to any disclaimer, the term of this patent is extended or adjusted under 35 U.S.C. 154(b) by 455 days.

This patent is subject to a terminal disclaimer.

(21) Appl. No.: 13/093,321

(22) Filed: Apr. 25, 2011

(65) Prior Publication Data

US 2011/0214512 A1 Sep. 8, 2011

Related U.S. Application Data

(63) Continuation-in-part of application No. 12/369,510, filed on Feb. 11, 2009, now Pat. No. 8,272,274.

(60) Provisional application No. 61/065,353, filed on Feb. 11, 2008, provisional application No. 61/131,307, filed on Jun. 6, 2008.

(51) Int. Cl.
*G01F 1/68* (2006.01)
(52) U.S. Cl.
USPC ........................................ 73/204.26
(58) Field of Classification Search
USPC ........................................ 73/204.26
See application file for complete search history.

(56) References Cited

U.S. PATENT DOCUMENTS

| 4,803,867 A | 2/1989 | Dahlin |
| 6,308,580 B1 | 10/2001 | Crisfield |
| 6,332,366 B1 | 12/2001 | Wray |
| 6,637,257 B2 | 10/2003 | Sparks |
| 6,647,778 B2 | 11/2003 | Sparks |
| 6,932,114 B2 | 8/2005 | Sparks |
| 7,059,176 B2 | 6/2006 | Sparks |

(Continued)

OTHER PUBLICATIONS

Peter Enoksson, Goran Stemme, and Erik Stemme; A Silicon Resonant Sensor Structure for Coriolis Mass-FLow Measurements; Journal of Microelectromechanical Systems, vol. 6, No. 2, Jun. 1997.

*Primary Examiner* — Jewel V Thompson
(74) *Attorney, Agent, or Firm* — Hartman Global IP Law; Gary M. Hartman; Demnica N. S. Hartman

(57) ABSTRACT

Fluidic systems and methods of determining properties of fluids flowing therein. The fluidic systems and methods make use of a micromachined device that determines at least one property of the fluid within the system. The micromachined device includes a base structure on a substrate and a tube structure extending from the base structure and spaced apart from a surface of the substrate. The tube structure has at least one pair of geometrically parallel tube portions substantially lying in a plane, and at least one continuous internal passage defined at least in part within the parallel tube portions. A drive element induces vibrational movement of the tube structure in the plane of the tube structure and induces resonant vibrational movements in the tube portions in the plane of the tube structure. A sensing element senses deflections of each tube portion in the plane of the tube structure.

40 Claims, 7 Drawing Sheets

(56) References Cited

U.S. PATENT DOCUMENTS

| | | |
|---|---|---|
| 7,228,735 B2 | 6/2007 | Sparks et al. |
| 7,263,882 B2 | 9/2007 | Sparks et al. |
| 7,354,429 B2 | 4/2008 | Sparks et al. |
| 7,437,912 B2 | 10/2008 | Sparks et al. |
| 2004/0171983 A1 | 9/2004 | Sparks et al. |
| 2005/0126304 A1 | 6/2005 | Sparks et al. |
| 2005/0235759 A1 | 10/2005 | Sparks et al. |
| 2005/0284815 A1 | 12/2005 | Sparks et al. |
| 2006/0211981 A1 | 9/2006 | Sparks et al. |
| 2007/0151335 A1 | 7/2007 | Sparks et al. |
| 2007/0157739 A1 | 7/2007 | Sparks et al. |
| 2008/0154535 A1 | 6/2008 | Sparks et al. |
| 2010/0037706 A1* | 2/2010 | Sparks et al. ............ 73/861.355 |

* cited by examiner

FLUIDIC SYSTEMS AND METHODS OF DETERMINING PROPERTIES OF FLUIDS FLOWING THEREIN

CROSS REFERENCE TO RELATED APPLICATIONS

This is a continuation-in-part patent application of co-pending U.S. patent application Ser. No. 12/369,510, filed Feb. 11, 2009, which claims the benefit of U.S. Provisional Application No. 61/065,353 filed Feb. 11, 2008, and U.S. Provisional Application No. 61/131,307 filed Jun. 6, 2008. The contents of these applications are incorporated herein by reference.

BACKGROUND OF THE INVENTION

The present invention generally relates to devices and methods for measuring properties of fluids. More particularly, this invention relates to fluidic systems equipped with a microfluidic device equipped with a resonating structure, a microchannel within the resonating structure through which a fluid of the fluidic system flows. The device is adapted to ascertain properties of the fluid while flowing through the microchannel. The performance of the device is improved by configuring the resonating structure to minimize mechanical losses resulting from the mechanical energy of the resonating structure being dissipated to a supporting substrate.

Fluid delivery devices capable of precise measurements find use in a variety of industries, nonlimiting examples of which include medical treatment systems such as drug infusion (delivery) and anesthetic delivery equipment, energy and fuel systems including fuel delivery systems and fuel cell systems such as direct methanol fuel cells (DMFC), chemical processing systems, and consumer goods. Various types of flow rate and concentration sensors have been proposed, including electrolytic, refractometer, ultrasonic, electrochemical, electromagnetic, and electromechanical sensors. An example of the latter is a Coriolis-based microfluidic device disclosed in commonly-assigned U.S. Pat. No. 6,477,901 to Tadigadapa et al., whose contents relating to the fabrication and operation of a Coriolis-based sensor are incorporated herein by reference.

Coriolis-based microfluidic devices of the type disclosed by Tadigadapa et al. include a micromachined tube supported above a substrate to have a freestanding portion. Drive and sensing electrodes are located on the substrate surface beneath the freestanding portion of the tube. The drive electrode can be, for example, capacitively coupled to the freestanding portion of the tube for capacitively (electrostatically) driving the freestanding portion at or near resonance, while the sensing electrodes sense (e.g., capacitively, optically, etc.) the deflection of the resonating tube relative to the substrate and provide feedback to enable the vibration frequency induced by the drive electrode to be controlled with appropriate circuitry. In use, while a fluid flows through an internal passage within the tube, the freestanding portion is vibrated at or near resonance by the drive electrode to ascertain certain properties of the fluid, such as flow rate and density, using Coriolis force principles. In particular, as the freestanding portion is driven at or near resonance by the drive electrode, the sensing electrodes sense a twisting motion of the freestanding portion, referred to as the Coriolis effect, about the axis of symmetry of the freestanding portion. The degree to which the freestanding portion twists (deflects) during a vibration cycle as a result of the Coriolis effect can be correlated to the mass flow rate of the fluid flowing through the tube, while the density of the fluid is proportional to the frequency of vibration at resonance.

Notable advantages of Coriolis-based microfluidic devices include the miniaturized scale to which they can be fabricated using semiconductor technology. As taught by Tadigadapa et al., the structural components of the device can be combined with electronics on a single chip by micromachining techniques, such as bulk etching and surface thin-film etching, to yield a microelectromechanical system (MEMS) capable of precisely analyzing very small quantities of fluids. When suitable miniaturized, a Coriolis-based microfluidic device can be enclosed by a capping wafer to allow for vacuum packaging that further improves the performance of the device by reducing air damping effects.

The microfluidic device disclosed in Tadigadapa et al. can be used in a wide variety of applications, as evident from commonly-assigned U.S. Pat. Nos. 6,637,257, 6,647,778, 6,932,114, 7,059,176, 7,228,735, 7,263,882, 7,354,429 and 7437912, U.S. Published Patent Application Nos. 2004/0171983, 2005/0126304, 2005/0284815, 2005/0235759, 2006/0211981, 2007/0151335, 2007/0157739, 2008/0154535, and pending U.S. patent application Ser. Nos. 12/031,839, 12/031,860, 12/106,642 and 12/143,942. As particular examples, U.S. Pat. No. 7,263,882 teaches that chemical concentrations, including those of fuel cell solutions, can be measured by sensing changes in fluid density as a fluid sample flows through a microchannel within a resonating tube of a MEMS-based Coriolis microfluidic device, and U.S. Published Patent Application No. 2007/0157739 teaches the capability of detecting potential measurement errors attributable to second phases such as gas bubbles in a fluid being evaluated by a resonating tube of a MEMS-based Coriolis microfluidic device.

While exhibiting very high sensitivity to mass flow rate, density and various other properties of a fluid, the performance of MEMS-based Coriolis microfluidic devices of the type taught by Tadigadapa et al. is subject to mechanical losses resulting from the attachment of the resonating tube to a substrate. In particular, clamping losses occur as a result of the tube's substrate anchor (attachment) to the MEMS substrate being stressed by tube displacement. A fraction of the vibration energy is lost from the tube though wave propagation into the MEMS substrate. While accounting for only a fraction of the vibration energy, clamping losses are sufficient that optimum performance requires a relatively large packaging mass to dissipate the mechanical energy loss and isolate the resonating tube from external mechanical stress and vibration. As such, further improvements in the sensitivities of MEMS-based Coriolis microfluidic devices are desired to fully realize the capabilities of these devices, especially if required to perform precise measurements in industries such as, for example, the medical, energy, fuel or chemical fields.

BRIEF DESCRIPTION OF THE INVENTION

The present invention provides fluidic systems and methods of determining properties of fluids flowing therein. The fluidic systems and methods make use of a micromachined device, and in particular a microelectromechanical system (MEMS) microfluidic device, and a method for operating the micromachined device to determine at least one property of the fluid within the system. The invention provides the capability of improving the performance of the micromachined device by minimizing clamping losses attributable to the attachment of a resonating tube to a substrate.

According to a first aspect of the invention, the fluidic system contains a micromachined device that includes a base structure on a substrate, and a tube structure extending from the base structure and spaced apart from a surface of the substrate. The tube structure has at least one pair of geometrically parallel tube portions substantially lying in a plane, at least one continuous internal passage defined at least in part within the parallel tube portions, and an inlet and outlet of the internal passage fluidically connected to the first base structure. The tube structure is configured for vibrational movement in the plane of the tube structure. At least one drive element is in proximity to the tube structure and is operable to induce the vibrational movement of the tube structure in the plane of the tube structure and to induce resonant vibrational movements in the tube portions in the plane of the tube structure. At least one sensing element is in proximity to the tube structure and is adapted to sense deflections of each of the tube portions in the plane of the tube structure when the tube structure is vibrated with the at least one drive element. At least a portion of the fluid in the fluidic system flows through the internal passage of the tube structure and at least one property of the fluid portion is determined with the micromachined device.

According to a second aspect of the invention, a method of determining at least one property of a fluid flowing in a fluidic system involves placing in the fluidic system a micromachined device having a tube structure comprising at least one pair of geometrically parallel tube portions substantially lying in a plane and at least one continuous internal passage defined at least in part within the parallel tube portions. At least one drive element is operated to induce vibrational movements in the tube structure as the fluid of the fluidic system flows through the internal passage within the tube structure so that the vibrational motion of the tube structure is parallel to the plane of the tube structure and the tube portions resonate about 180 degrees out of phase with each other. Deflections of each of the tube portions are sensed in the plane of the tube structure, outputs are produced corresponding to the sensed deflections, and from the outputs the at least one property of the fluid is determined.

According to a preferred aspect of the invention, the vibrational movements of the parallel tubes are preferably about 180 degrees out of phase with each other to minimize the mechanical (clamping) losses that must be dissipated to the substrate. This aspect of the invention can be utilized to promote the sensitivity of the MEMS device, and/or allow for the use of packaging processes and materials that are less expensive that conventional MEMS devices. According to another preferred aspect of the invention, the parallel tubes are preferably configured and driven so as to reduce squeeze film damping, which often necessitates vacuum packaging of MEMS Coriolis-based microfluidic sensors. The fluidic system in which the micromachined device is installed can be of a variety of types, including medical treatment systems, energy and fuel systems, chemical mixing systems, chemical processing systems, and consumer goods, which may utilize a wide variety of fluids, including liquids, gases, solutions, colloids, suspensions and mixtures thereof. Finally, the micromachined device can be fabricated as a disposable unit of the fluidic system, such that the micromachined device can be removed from the system and replaced by another device. Such a capability is especially useful in fluidic systems that are intended for multiple uses, but in which the micromachined device is susceptible to becoming contaminated by the fluid being analyzed by the device within the system.

Other objects and advantages of this invention will be better appreciated from the following detailed description.

DETAILED DESCRIPTION OF THE INVENTION

Figure 1:
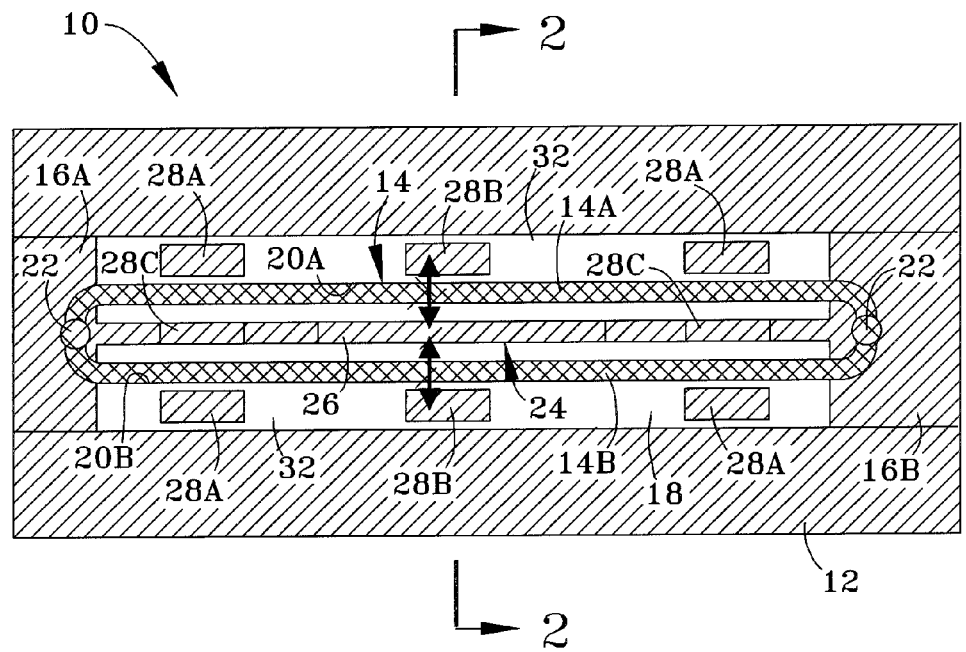
FIG. 1 is a plan view of a microfluidic device with a micromachined structure comprising a pair of parallel tube portions bridging a cavity and a drive structure between the tube portions for electrostatically vibrating the tube portions in accordance with a first embodiment of this invention.

FIGS. 1 through 9 represent micromachined devices 10, and in particular microelectromechanical system (MEMS) microfluidic devices, that are suitable for use in fluidic systems where accuracy and precision are important. Notable examples include chemical concentration applications, including but not limited to medical treatment systems such as drug mixing equipment, drug infusion (delivery) equipment, anesthetic delivery equipment and blood purification equipment, energy and fuel systems including fuel delivery systems and fuel cell systems such as direct methanol fuel cells (DMFC), chemical mixing systems, chemical processing systems, and consumer goods. In such applications, the micromachined devices 10 may be employed to determine various properties of fluids within a fluidic system, for example, mass flow rate, density, specific gravity, volumetric flow rate, dose, total volume delivered, temperature, chemical concentration, viscosity, and lubricity.

In FIGS. 1 through 9, consistent reference numbers are used to identify functionally equivalent structures. As will be discussed below, the devices 10 are similar in construction and operation to the MEMS microfluidic device disclosed by Tadigadapa et al., but modified to exhibit improved operating characteristics. Each device 10 is represented in FIGS. 1 through 9 as being fabricated on a substrate 12, which may be a wafer-level component or part of a package to which micromachined components of the device 10 are attached. Depending on the application, construction, and packaging of the device 10, the substrate 12 is preferably formed of a plastic, metal, glass or ceramic material. Other potential materials for the substrate 12 include silicon, doped silicon or another semiconductor material, quartz, a composite material, or another material capable of being micromachined. A tube structure 14 is supported from at least one base structure 16 bonded to the substrate 12, such that the tube structure 14 is supported above a surface 18 of the substrate 12. The tube structure 14 and its base structure 16 can be formed of a variety of materials, including but not limited to silicon, doped silicon and other semiconductor materials, diamond, metals (for example, tungsten, copper, aluminum, platinum, titanium, tantalum and other commonly deposited film materials), dielectric materials including glass, plastic and ceramic materials (for example, silicon carbide), and other materials capable of being micromachined. Depending on the particular construction of the device 10, the substrate surface 18 beneath the tube structure 14 may be defined by one or more recesses in the substrate 12 or any other manner to define a gap between the tube structure 14 and substrate 12.

Figure 3:
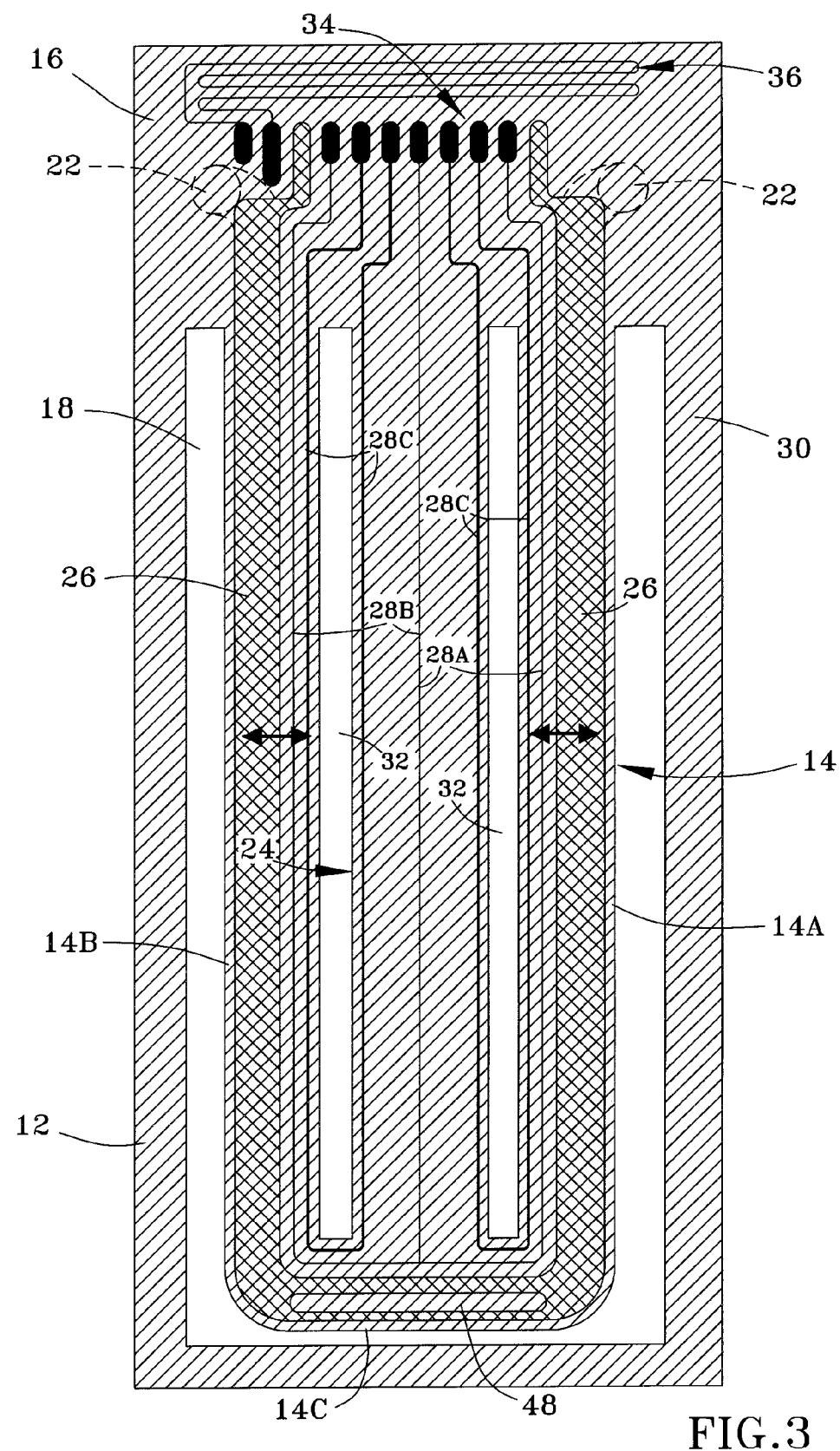
FIG. 3 is a plan view of a microfluidic device with a micromachined cantilevered structure comprising a U-shaped tube structure and a sensing structure surrounded by and attached to the tube structure, wherein the tube structure is adapted to be magnetically or electromagnetically vibrated and the sensing structure is adapted to sense vibration of the tube structure in accordance with a fourth embodiment of this invention.

FIGS. 1, 3, 6, and 8 are plan views of the devices 10, and depict the tube structure 14 as capable of having a variety of shapes. The embodiments represented in FIGS. 1, 3, 6 and 8 share in common the presence of a tube portion, and more preferably at least a pair of parallel tube portions 14A and 14B, as part of their tube structures 14. The tube portions 14A and 14B of the devices 10 shown in the Figures preferably lie in a plane that is substantially parallel to the substrate surface 18 over which they are suspended. The tube structures 14 of FIGS. 1, 6, and 8 bridge the substrate surface 18 between two portions 16A and 16B of the base structure 16, whereas the tube structure 14 in FIG. 3 is cantilevered above the substrate surface 12. Each tube structure 14 defines at least one continuous internal passage through which a fluid (a gas, liquid, or gas-liquid mixture) can flow. In FIG. 1, the parallel tube portions 14A and 14B define a pair of parallel passages 20A and 20B that are also fluidically in parallel, while in FIGS. 3 and 6 the parallel tube portions 14A and 14B define a pair of geometrically parallel passages 20A and 20B that are fluidically in series to define a continuous internal passage 20 within the tube structure 14. Other configurations—both simpler and more complex—are foreseeable for the tube structures 14 and their internal passages 20, 20A and 20B.

In the embodiments shown in the Figures, fluid enters and exits the tube structure 14 via a pair of ports 22 located in the base structure 16, either of which can serve as an inlet or outlet for fluid flow through the passages 20A and 20B. Consistent with the teachings of Tadigadapa et al., the tube structures 14 of FIGS. 1 through 8 are intended to be vibrated at or near the resonant frequency of the tube portions 14A and 14B to determine the mass flow rate and density of the fluid flowing through the tube structure 14 using Coriolis force principles. However, in contrast to the teachings of Tadigadapa et al., each of the tube structures 14 shown in the Figures is configured and adapted so that its vibrational movement is in a direction parallel to the plane in which it lies and parallel to the substrate surface 18, instead of in a direction perpendicular to their plane and the substrate surface 18. Furthermore, the tube portions 14A and 14B have at least one the vibration mode in which their resonant vibrational movements are in the plane of the tube structure (14) and about 180 degrees out of phase with each other.

The shape and size of each tube structure 14 and its tube portions 14A and 14B and passages 20A and 20B can be chosen to provide an adequate flow capacity for the fluid(s) to be evaluated with the device 10, as well as suitable vibration parameters. In addition, the wall thicknesses of the tube portions 14A and 14B can be adapted to accommodate various fluid pressure levels, including greater wall thicknesses for high pressure fluid applications. The tube structure 14, base structure 16 and internal passages 20, 20A and 20B are preferably formed by micromachining, which is known and used herein to refer to techniques for forming very small elements by bulk etching a substrate (e.g., a silicon wafer) or by surface thin-film etching, the latter of which generally involves depositing a thin film (e.g., polysilicon or metal) on a sacrificial layer (e.g., oxide layer) on a substrate surface and then selectively removing portions of the sacrificial layer to free the deposited thin film. The tube structure 14 and base structure 16 can either be fabricated entirely from layers of the chosen materials deposited on or bonded to the substrate 12, or fabricated in part by etching the substrate 12. Because micromachining technologies are employed to fabricate the tube structure 14, the size of the tube structure 14 and its internal passages 20, 20A and 20B can be extremely small, such as tube lengths of about 0.5 mm or less and passage widths of ten to one thousand micrometers, with smaller and larger tubes and passages also being within the scope of this invention.

Particularly suitable processes for fabricating the devices 10 of this invention using micromachining techniques are disclosed in commonly-assigned U.S. Pat. No. 6,477,901 to Tadigadapa et al., commonly-assigned U.S. Pat. No. 6,647,778 to Sparks, and commonly assigned U.S. Pat. No. 7,381,628 to Sparks et al., whose disclosures relating to micromachining processes are incorporated herein by reference. Also within the scope of this invention are tube structures 14 produced by electroplating, electroless plating, sputtering, and evaporating metals, and the use of dielectric layers and sacrificial layers to form the internal passages 20, 20A and 20C of the tube structures 14. Dielectric layers can remain on the tube structure 14 to provide electrical insulation for subsequent layers built up on the tube structures 14 that, as described in more detail below, will serve as means for actuating the tube structures 14 and sensing vibration of the tube structures 14. Finally, it is also within the scope of the invention to construct the tube structure 14 of metal, glass, polymer or ceramic materials, to which metal wires, runners, or circuit traces are attached to serve as actuating and/or sensing means. For example, vibration of a tube structure 14 formed of a metallic material could be induced with a flex circuit bonded to the tube structure 14.

Because of their miniature size, the micromachined tube portions 14A and 14B shown in FIGS. 1 through 9 can be used to very accurately determine the mass flow rate and density of a fluid flowing through the tube structure 14. As such, the devices 10 are suitable for use in a wide variety of applications where accuracy and precision are important, such as chemical concentration applications including but not limited to medical treatment systems, energy and fuel systems including fuel delivery systems and fuel cell systems, chemical mixing systems, chemical processing systems, and consumer goods. Coriolis force principles can also be used to ascertain the viscosity, lubricity, and other properties of a fluid flowing through the tube structure 14.

Figure 2:
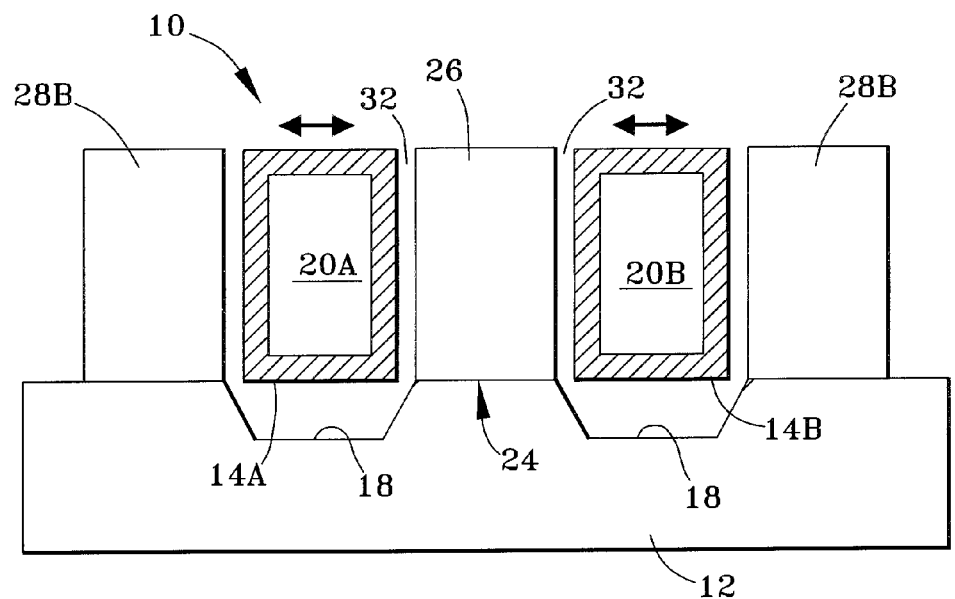
FIG. 2 is a cross-sectional view of the microfluidic device of FIG. 1.

With particular reference to FIGS. 1 and 2, an embodiment of the device 10 is represented in which the tube structure 14 is configured so that the tube portions 14A and 14B individually bridge the substrate surface 18 in parallel between two portions 16A and 16B of the base structure 16, and a such have a substantially linear or straight shape. During half of the vibration cycle in which the tube structure 14 travels upward, each tube portion 14A and 14B has upward momentum as the fluid travels therethrough, the fluid entering the tube structure 14 resists the vertical upward motion of the tube structure 14 by pushing downward on the tube portions 14A and 14B near the port 22 serving as the fluid inlet, and the fluid exiting the tube structure 14 resists having its upward vertical motion (acquired from the tube structure 14) decreased by pushing upward on the tube portions 14A and 14B near the port 22 serving as the fluid outlet. The resulting forces cause deflections of the tube portions 14A and 14B near the inlet port 22 to lag behind the deflections of the tube portions 14A and 14B near the outlet port 22. This lag during a vibration cycle is the result of the Coriolis effect and can be correlated to the mass flow rate of the fluid flowing through the tube structure 14, while the density of the fluid is proportional to the frequency of vibration at resonance.

Though necessary to the operation and sensing technique used by the MEMS devices 10, the twisting motion of the tube structure 14 applies mechanical stresses to the attachment between the tube structure 14 and base structure 16, resulting in clamping losses that must be dissipated to the substrate 12 and any additional packaging in which the device 10 is enclosed. A desired aspect of the invention is to reduce these losses by causing the tube portions 14A and 14B to vibrate in the same plane in which the tube structure 14 lies, as indicated by the arrows in FIGS. 1 and 2. By configuring the tube structure 14 so that the tube portions 14A and 14B vibrate approximately 180 degrees out of phase with each other, mechanical losses dissipated to the substrate 12 are minimized. The ability to minimize mechanical losses improves as the masses of the tube portions 14A and 14B become closer, with optimal results believed to occur when the masses of the tube portions 14A and 14B are approximately equal. The resonant frequencies of the tube portions 14A and 14B are influenced by their mechanical design (shape, size, mass, construction and materials), which can be optimized for a particular application using, for example, known finite element modeling. For many applications, suitable resonant frequencies will generally be in a range of about 1 kHz to about 150 kHz.

The relative amplitudes of vibration for the tube portions 14A and 14B will also be determined by their mechanical design, while amplitude as a whole can be adjusted through the means used to vibrate the tube structure 14. For this purpose, FIGS. 1 and 2 show a drive element 26 formed as part of a platform 24 on the substrate 12 between the tube portions 14A and 14B of the tube structure 14. The drive element 26 can be formed of any suitable material, such as doped silicon or metal. If also formed of an electrically-conductive material, such as doped silicon or metal, the tube structure 14 can capacitively couple with the drive element 26, enabling the element 26 to electrostatically drive the tube structure 14. However, it is foreseeable that the tube structure 14 could be formed of a nonconductive material, and a separate electrode formed on the tube structure 14 facing the element 26 for vibrating the tube structure 14 electrostatically. Because electrostatic coupling improves with proximity, the gap 32 between the tube portions 14A and 14B are preferably on the order of about one to about five micrometers, though lesser and greater gaps are foreseeable. To achieve a uniform narrow gap 32, the tube structure 14 and platform 24 are preferably defined by reactive ion etching (RIE) or plasma etching, though it is foreseeable that wet etching and other techniques could be used to define the walls of the tube structure 14 and platform 24. As will be discussed in reference to other embodiments of the invention, greater gap widths become practical with other techniques for driving the tube structure 14 of FIGS. 1 and 2, including magnetic, piezoelectric, piezoresistive, thermal and optical.

Figure 10:
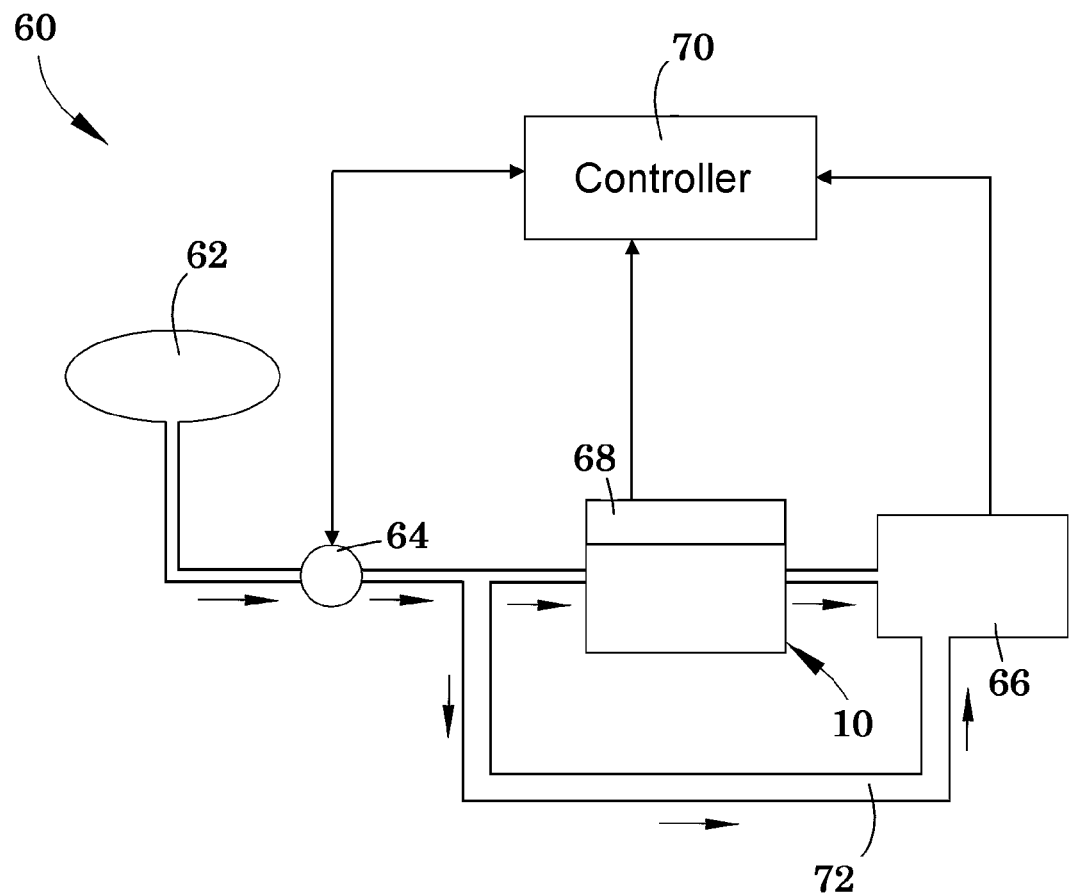
FIG. 10 schematically represents one of the devices of FIGS. 1 through 8 installed in a fluidic system for performing accurate and precise measurements of one or more properties of a fluid in the system.

The Figures further show sensing elements 28A, 28B and 28C arranged in pairs to sense the deflection of the tube structure 14 relative to the substrate 12, and to provide feedback to the drive element 26 to enable the vibration frequency to be controlled with any suitable on-chip or remote microprocessor or microcontroller (FIG. 10). The sensing elements 28A-C can sense the proximity or motion of the adjacent tube portion 14A or 14B capacitively, electrostatically, magnetically, electromagnetically, piezoelectrically, piezoresistively, thermally, optically, or in any other suitable manner capable of sensing the proximity or motion of the tube structure 14. The deflection along the length of each tube portion 14A and 14B as a result of the Coriolis effect are preferably detected by the sensing elements 28A, while the vibration frequency is preferably detected by the sensing elements 28B. While shown separated from the tube structure 14 by a lateral gap parallel to the direction of vibration of the tube structure 14, the sensing elements 28A and 28B could be placed under the tube structure 14 in close alignment to the edge of the tube structure to sense lateral motion as the tube structure 14 moves over and then away from the elements 28A and 28B. The remaining sensing elements 28C are shown as located on the platform 24 and can be utilized as additional sensing electrodes or as balancing electrodes to compensate for errors leading to output errors and drift due to processing differences across the tube structure 14, packaging-related stresses, and aging effects. Input and output signals to the drive and sensing elements 26 and 28A-C can be made through bond pads (not shown) along an edge of the substrate 12, and transmitted to the microcontroller with appropriate amplification and signal conditioning circuitry as well known in the art.

As previously noted, a preferred aspect of the invention is to reduce mechanical losses by vibrating the tube portions 14A and 14B in approximately the same plane (the plane of the tube structure 14) and about 180 degrees out of phase with each other. The reduced mechanical losses made possible with this invention potentially enable the device 10 to be fabricated or mounted on acoustically lossy materials such as less expensive plastic substrates, and/or packaged in plastic packages and/or over molded to reduce product costs. In particular preferred embodiments, the substrate 12 and/or the tube structure 14 are formed from one or more plastic materials, which allow for the entire device 10 to be manufactured and used as a disposable unit. Reduced mechanical losses also offer the possibility of the sensor package being able to withstand greater mechanical stresses without adversely impacting the performance of the device 10.

As noted above, the tube structure 14 of FIGS. 3 and 4 differs in part from the embodiment of FIGS. 1 and 2 as a result of being cantilevered above the substrate surface 12. In addition, the tube portions 14A and 14B are geometrically parallel but fluidically in series and anchored adjacent each other to the base structure 16. The continuous internal passage 20 defined by the tube structure 14 is represented as having a U-shaped configuration, though other shapes are also possible. As evident from FIG. 3, the platform 24 is physically connected to a distal end 14C of the tube structure 14. In this manner, the sensing elements 28A-B and balance elements 28C can be routed around the perimeters of the gaps 32 between the platform 24 and the tube portions 14A and 14B, while the drive element 26 remains on the tube structure 14. An optional frame 30 surrounds the cantilevered tube structure 14 and platform 24. The frame 30 improves handling of the device chip during fabrication and provides surfaces on which metal traces or runners can be formed. In combination with the base structure 16, the frame 30 also provides additional protection to the tube structure 14 and platform 24 during fabrication and handling. Though also possible without the frame 30, the protection offered by the frame 30 can eliminate any need for the tube structure 14 to be cantilevered above the substrate 12. Instead, the base structure 16 can be attached to the substrate 12 by an adhesive, solder, or other attachment method, with only the tube structure 14 and (optionally) the frame 30 cantilevered outward away from the substrate 12. Such an entirely cantilevered tube structure 14 (and frame 30) provides the capability for improved performance over wide temperature ranges, and prevents or at least significantly reduces packaging stresses attributable to flexing of the device 10 due to the various materials of the device 10 having different coefficients of thermal expansion.

Figure 4:
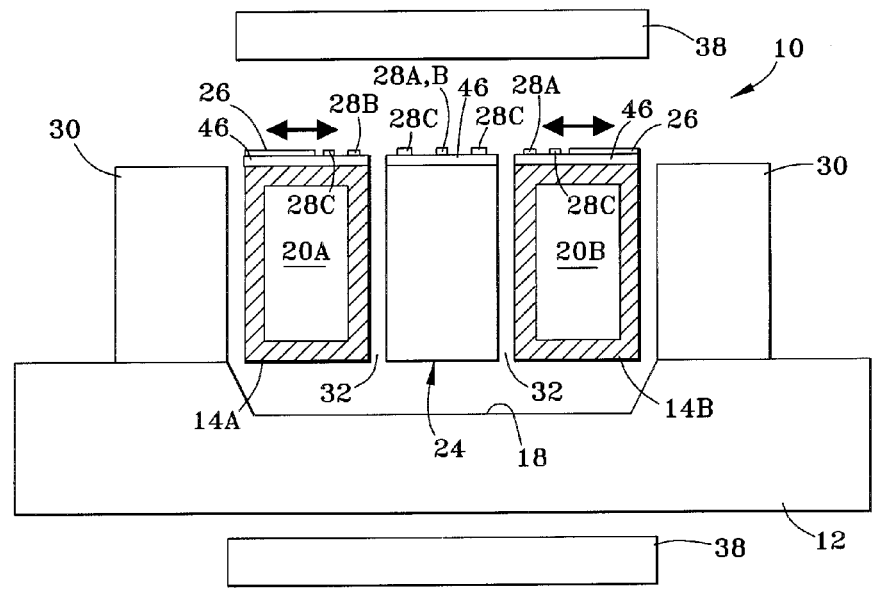
FIG. 4 is a cross-sectional view of the microfluidic device of FIG. 3.

According to a preferred aspect of the embodiment of FIGS. 3 and 4, while various driving techniques may be used, including electrostatic, piezoelectric, thermal, piezoresistive, optical, and other actuation techniques, the tube structure 14 is preferably driven magnetically. For example, FIG. 3 shows the drive elements 26 as metallic traces or runners (e.g., aluminum or another suitable conductive material) on the upper surface of the tube structure 14 for vibrating the tube structure 14 electromagnetically with the use of one or more magnetic field sources 38 (for example, electromagnets or permanent magnets) positioned above and/or below the tube structure 14 (FIG. 4). As known in the art, magnetic actuation schemes of this type make use of the Lorentz force.

When electrical current is passed through the drive element 26 while subjected to a magnetic field, each moving charge of the current experiences the Lorentz force. In the case of the straight segments of the drive element 26 of FIG. 3, the Lorentz force can be calculated as follows:

$$F = lL \times B$$

where F is force (measured in newtons), $l$ is current in the drive element 26 (measured in amperes), B is the magnetic field vector (measured in teslas), x is the vector cross product, and L is a vector whose magnitude is the length of the drive element 26 (measured in meters) and whose direction is along the drive element 26 aligned with the direction of conventional current flow.

The sensing elements 28A and 28B are also shown in the form of metallic traces or runners (e.g., aluminum or another suitable conductive material) placed on the upper surface of the platform 24 for electromagnetically sensing the movement of the tube structure 14. The sensing elements 28A and 28B are represented as disposed along the lateral edges of the platform 24 in proximity to the tube structure 14 for electromagnetically coupling with the drive element 26. The drive and sense elements 26 and 28A-B are shown connected to bond pads 34, which can be formed in the same metal layer as that used to form the elements 26 and 28. As with the embodiment of FIGS. 1 and 2, alternative sensing techniques include capacitive, electrostatic, piezoelectric, piezoresistive, thermal, optical, and other suitable methods capable of sensing the proximity or motion of the tube structure 14. Likewise, the electromagnetic drive and sensing scheme of FIGS. 3 and 4 could be employed with the device structure of FIGS. 1 and 2.

By passing current through the drive element 26, vibration can be induced in the tube structure 14. More particularly, under the influence of a sinusoidal or alternating magnetic field applied by the one or more magnetic field sources (electromagnets) 38, the tube portions 14A and 14B are caused to move laterally outward away from each other and then move laterally inward toward each other during each complete vibration cycle. The sensing elements 28A-B detect vibration of the tube structure 14 by detecting a voltage generated across the drive element 26 as it moves in the perpendicular magnetic field. A ring pole (not shown) can be employed to concentrate the magnetic field on the tube structure 14. Depending on the material of the tube structure 14, the drive element 26 can be fabricated on a dielectric layer 46 (e.g., silicon dioxide) on the surface of the tube structure 14 to provide electrical insulation therebetween.

It should be noted that if a drive and/or sensing scheme other than electromagnetic is employed, for example, electrostatic, piezoelectric, thermal, piezoresistive, optical, etc., the drive and sensing elements 26 and 28 may be configured differently from what is shown in FIGS. 3 and 4 and formed of different materials. For example, in the case of a piezoelectric actuation/sensing scheme, piezoelectric materials such as aluminum nitride, lead zirconate titanate (PZT), quartz, or another piezoelectric material would be incorporated as elements into the conductive runners shown for the drive and sensing elements 26 and 28 in FIGS. 3 and 4. What is known as the reverse piezoelectric effect can then be utilized by one or more drive elements 26 to produce vibration-inducing alternating stresses/strains in the tube structure 14 in response to an applied electric field, and the direct piezoelectric effect can be used by one or more sensing elements 28 to produce an electrical signal in response to flexing of the tube structure 14 when vibrated.

The accuracy of measurements made with any of the devices 10 shown in FIGS. 1 through 8 can be improved by monitoring the temperature of the fluid flowing through the tube structure 14. For this purpose, the device 10 is shown in FIG. 3 as equipped with a temperature sensing element 36. A suitable construction for the sensing element 36 can make use of the same metal layer that forms the drive and sensing elements 26 and 28 and their associated bond pads 34, or one or more additional metal layers of the type used to form the drive and sensing elements 26 and 28 and bond pads 34. For example, a resistive-based temperature sensing element 36 can be formed by a thin-film metal layer of gold, platinum, palladium, chromium, nickel, aluminum, polysilicon, or another conductive material in accordance with known practices. Furthermore, either of the drive and sensing elements 26 and 28 could be used as a thin film temperature sensing element in place of the dedicated temperature sensing element 36 shown in the Figures. With the temperature sensing element 36, changes in mechanical properties of the tube structure 14 and properties of the fluid therein attributable to temperature changes can be compensated for with signal conditioning circuitry. While depicted in FIG. 3 as being on the base structure 16 near the tube structure 14, it is foreseeable that the temperature sensing element 36 could be fabricated on the frame 30 or on the tube structure 14 (FIGS. 8 and 9) to obtain more accurate readings of the fluid temperature.

Figure 5:
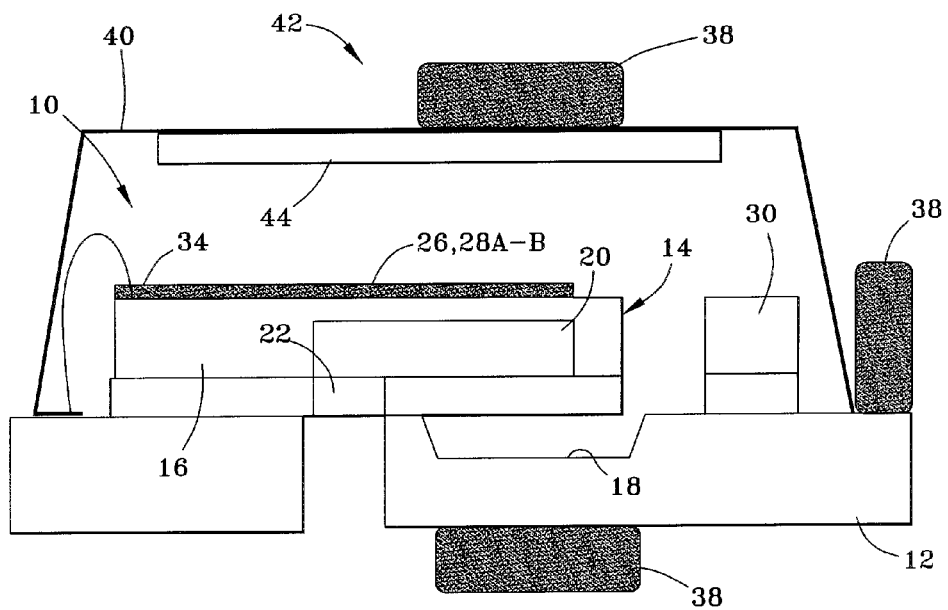
FIG. 5 is a cross-sectional view of the microfluidic device of FIGS. 3 and 4 enclosed in a housing configured for magnetically or electromagnetically vibrating the parallel tube portions.

FIG. 5 represents the device 10 of FIGS. 3 and 4 enclosed by a cap 40 to form a sensing package 42. Depending on its construction and material, the use of a cap 40 preferably inhibits dust and chemical corrosion of the device 10 and its components and may allow for vacuum packaging that reduces air damping of the tube vibration. A variety of package and wafer-level methods exist for sensor packages, including vacuum package devices. These include solder or weld hermetic packages, and wafer bonding using glass frit, solder, eutectic alloy, adhesive, and anodic bonding. Silicon is a particular example of a suitable material for the cap 40, which has the advantage of allowing silicon-to-silicon bonding techniques to be used, though it is foreseeable that a variety of other materials could be used, including metals and glass materials, the latter including borosilicate glass (e.g., Pyrex). The cap 40 may enclose a printed circuit board or ASIC to which the outputs of the device 10 can be wirebonded or otherwise electrically connected.

FIG. 5 depicts three of the various possible locations for the magnetic field sources 38. For use in combination with the metallic drive and sensing elements 26 and 28A-B of FIGS. 3 and 4, the magnetic field sources 38 can be permanent magnets or magnet-core combinations. Alternatively, FIG. 3 further depicts a thin film 48 of magnetic material placed on the upper surface of the tube structure 14 for use in combination with electromagnets 38 to generate alternating Lorentz forces that induce vibration in directions parallel to the plane of the structure 14. Suitable magnetic materials for the film 48 include ferromagnetic materials and alloys, iron, nickel, cobalt, and their alloys, Fe—Si alloys, KOVAR® (a nickel-cobalt ferrous alloy commercially available from Carpenter Technology Corporation), soft steels, mu-metal (nickel-iron alloy), metal silicides, Fe—Si—Al alloys, rare earth magnetic materials, ferrites and other suitable magnetic materials. Various methods can be employed to form the magnetic film 48, including shadow masks, photolithography, mask and etch, liftoff processing, etc. The magnetic film 48 can be deposited by such nonlimiting methods as evaporation, sputtering, plating and combinations of these and other methods. Adhesion of the magnetic film 48 may be promoted with a silicide formation or another suitable material. The film 48 may be annealed and/or poled to improve its performance. Core materials can be used to further focus the magnetic field on the magnetic film 48. For example, a C- or U-shaped core made of iron or other similar material may include a permanent magnet and the device 10 in its path.

Electromagnets suitable for use as magnetic field sources 38 can be of any suitable type, including rod-type core and C-shaped ferrite or iron core electromagnets. Magnetic field sources 38 located above and below the tube structure 14 induce lateral vibration in the structure 14 by generating a magnetic field that is substantially perpendicular to the vibrational plane of the tube structure 14. Alternatively or in addition, FIG. 5 shows a magnetic field source 38 to the side of the tube structure 14, roughly in the plane of the tube structure 14. This location for a magnetic field source 38 may improve the phase separation of the device 10 for flow detection, particularly if the tube structure 14 includes a ferrite material. In the form of an electromagnet, a magnetic field source 38 may form part of a phase-lock-loop circuit to maintain the tube structure 14 at its resonant frequency over time and temperature variations.

In certain embodiments of the invention in which a vacuum is desired within the sensor package 42, the bond between the cap 40 and substrate 12 is hermetic and the resulting enclosure is evacuated to enable the tube structure 14 to be driven efficiently at high quality (Q) factor values without damping. In such an embodiment, a getter material 44 is preferably placed in the enclosure to assist in reducing and maintaining a low cavity pressure. It is foreseeable that the role of the getter material 44 could be supplanted by an appropriate choice of material for the magnetic film 48, eliminating the need for a separate metal deposition step to form the getter material 44. As an alternative to a hermetically sealed package, the tube structure 14 could be enclosed such that a vacuum can be drawn when desired through the use of a pump.

It should be noted that, because the use of a magnetic actuation scheme to drive the tube structure 14 allows for larger gaps 32 between the tube structure 14 and its drive and sensing elements 26 and 28A-B, squeeze film damping may be sufficiently reduced to eliminate the need for vacuum packaging of the device 10. A benefit of this is the ability to reduce the mass of the tube structure 14 by thinning the sidewalls of the tube portions 14A and 14B, thereby increasing the sensitivity of the device 10 to density or chemical concentration measurements. Thinning of the sidewalls can be achieved by performing additional isotropic or anisotropic etching after the walls of the tube structure 14 have been defined. This step can be performed as part of the standard process for fabricating the device 10, or interactively after the device 10 has been tested to determine its resonant frequency.

In view of the above, it should be understood that the hermetic package 42 shown in FIG. 5 may be appropriate or desirable for the device 10 of FIGS. 1 and 2, whose electrostatic sensing technique necessitates narrower gaps 32 between the tube structure 14 and its drive and sensing elements 26 and 28A-C. Furthermore, though not necessarily required for vacuum packaging, enclosure of the device of FIGS. 3 and 4 will often be desirable to prevent dust and chemical corrosion of the device 10 and its components.

Figure 6:
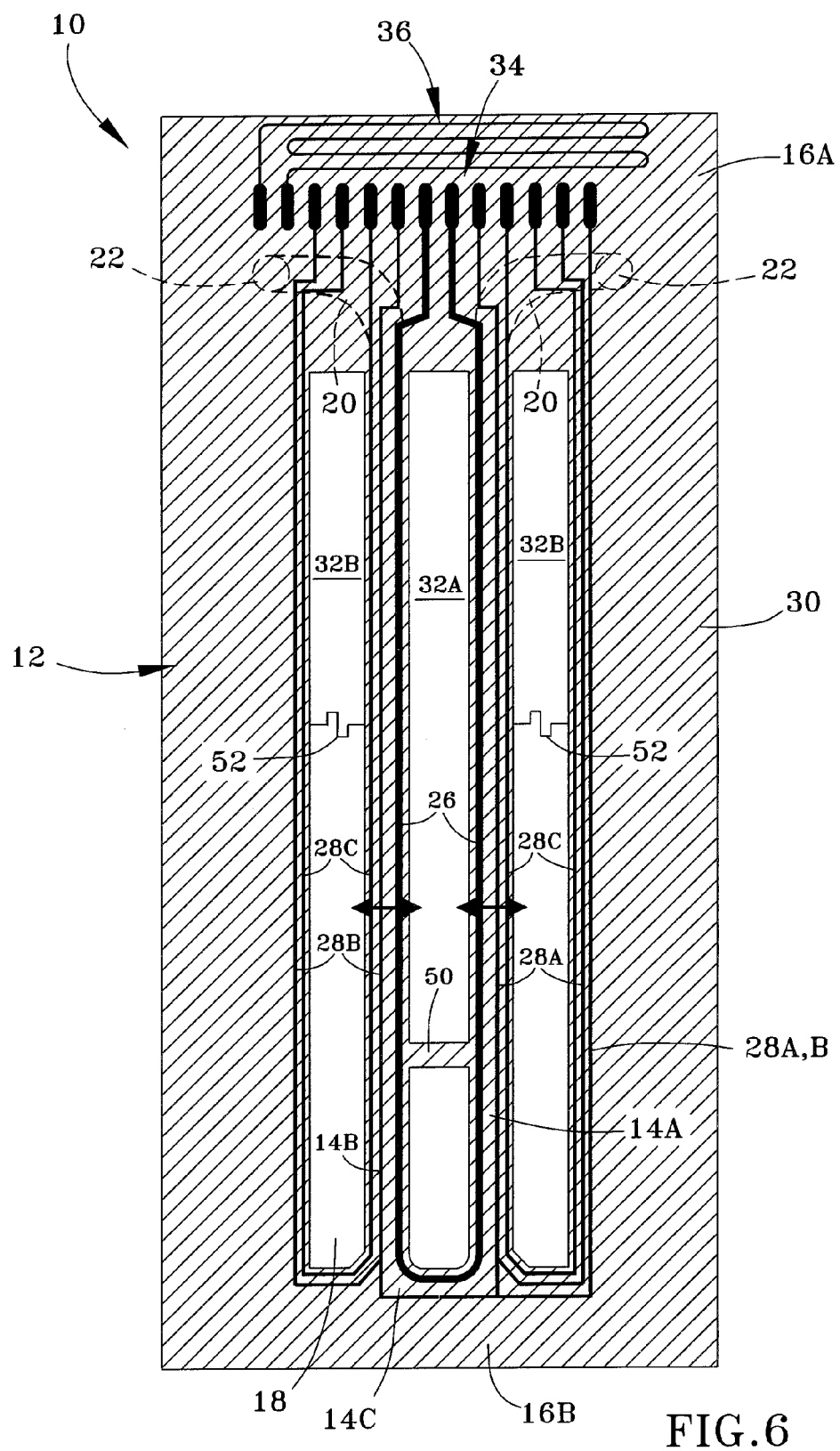
FIG. 6 is a plan view of a microfluidic device with a micromachined bridge structure comprising a pair of parallel tube portions bridging a cavity, wherein the tube portions are adapted to be electromagnetically vibrated and sensing elements are on and surround the tube portions to sense vibration of the tube portions in accordance with a fifth embodiment of this invention.
Figure 7:
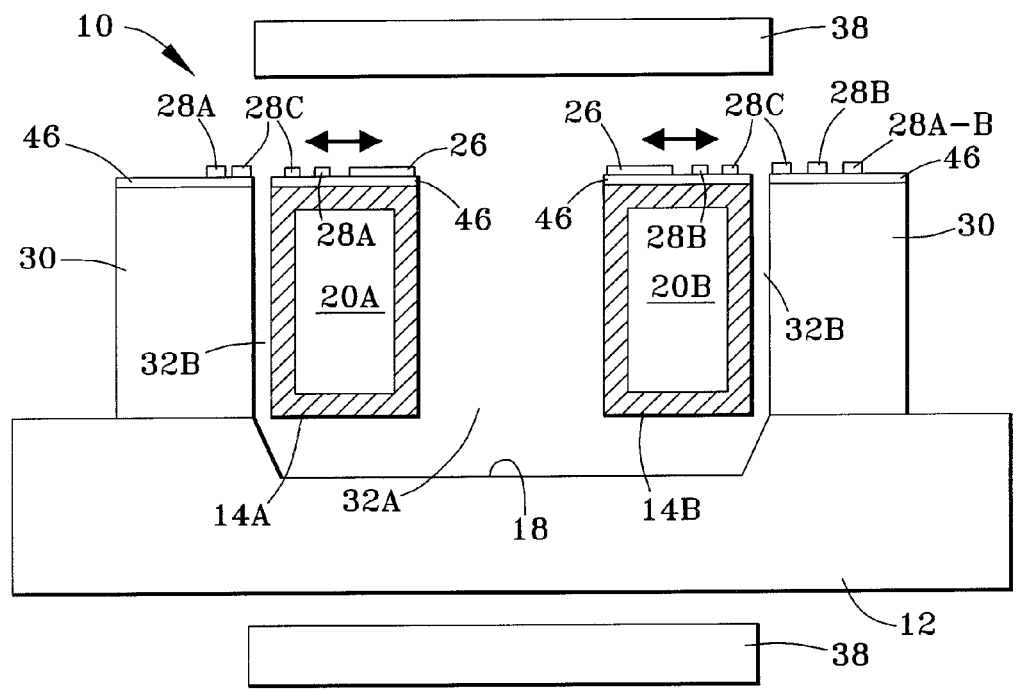
FIG. 7 is a cross-sectional view of the microfluidic device of FIG. 6.

With reference to FIGS. 6 and 7, a device 10 is shown with a tube structure 14 whose tube portions 14A and 14B bridge the substrate surface 18, similar to the bridge-type embodiment of FIGS. 1 and 2. The distal end 14C of the tube structure 14 is physically connected to the base structure 16, with the result that the FIGS. 6 and 7 represent another bridge-type embodiment of the invention. The device 10 differs in one respect by the drive and sensing elements 26 and 28A-B being in the form of runners for electromagnetic actuation, similar to the embodiment of FIGS. 3 and 4. Furthermore, the platform 24 has been eliminated, with the result that the parallel tube portions 14A and 14B are spaced apart from each other by a single gap 32A therebetween, and the gap 32B across which sensing occurs is outside the tube structure 14 (similar to FIG. 1) instead of inside the tube structure 14 (as is the case with FIG. 3). In addition, an optional stiffening bridge 50 is provided between and connects the tube portions 14A and 14B, and optional springs 52 are provided between and connect the tube portions 14A and 14B to the frame 30 surrounding the tube structure 14. In this manner, the resonant frequency and/or mode of the tube structure 14 can be modified by appropriately sizing and locating the stiffening bridge 50 and more flexible springs 52 during fabrication of the tube structure 14, during which the tube structure 14, bridge 50 and springs 52 can be simultaneously defined by etching. Under appropriate conditions, it is foreseeable that the locations of the stiffening bridge 50 and springs 52 could differ from what is shown in FIG. 6, or their locations switched, or only one or more bridges 50 or one or more springs 52 may be used.

Figure 8:
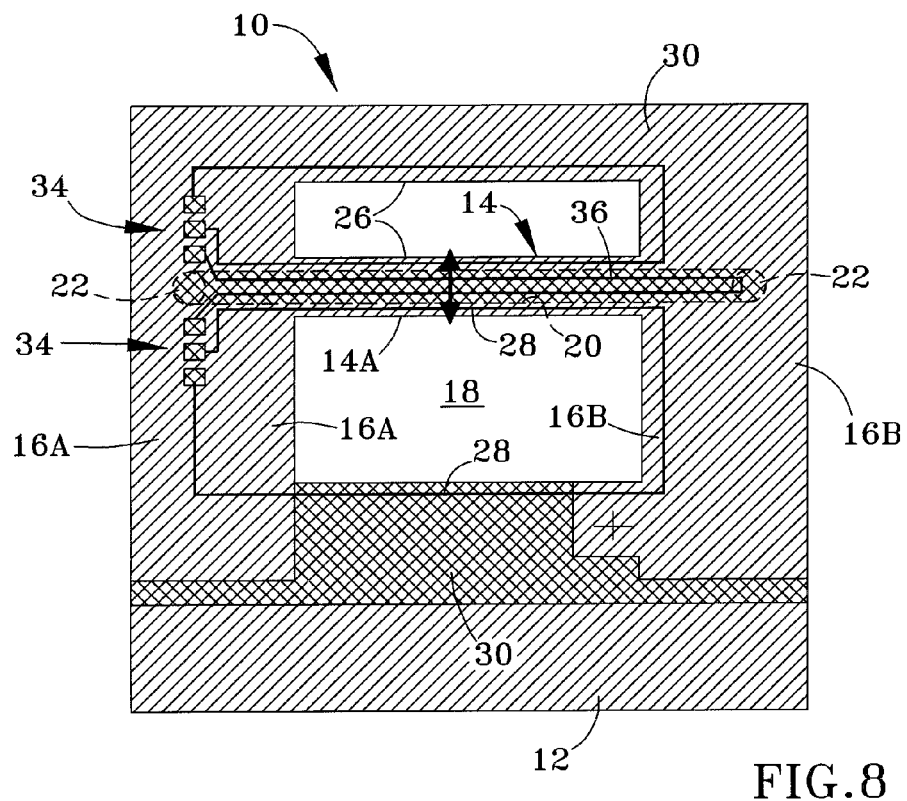
FIG. 8 is a plan view of a microfluidic device with a micromachined structure comprising a single tube portion bridging a cavity and adapted to be electromagnetically vibrating in accordance with a seventh embodiment of this invention.

FIG. 8 depicts a bridge-type embodiment similar to FIGS. 1 and 6, but with a single tube portion 14A on which both drive and sensing elements 26 and 28 are located. As previously noted in reference to FIG. 3, FIG. 8 shows the temperature sensing element 36 on the tube portion 14A to obtain a more accurate temperature reading of the fluid.

Figure 9:
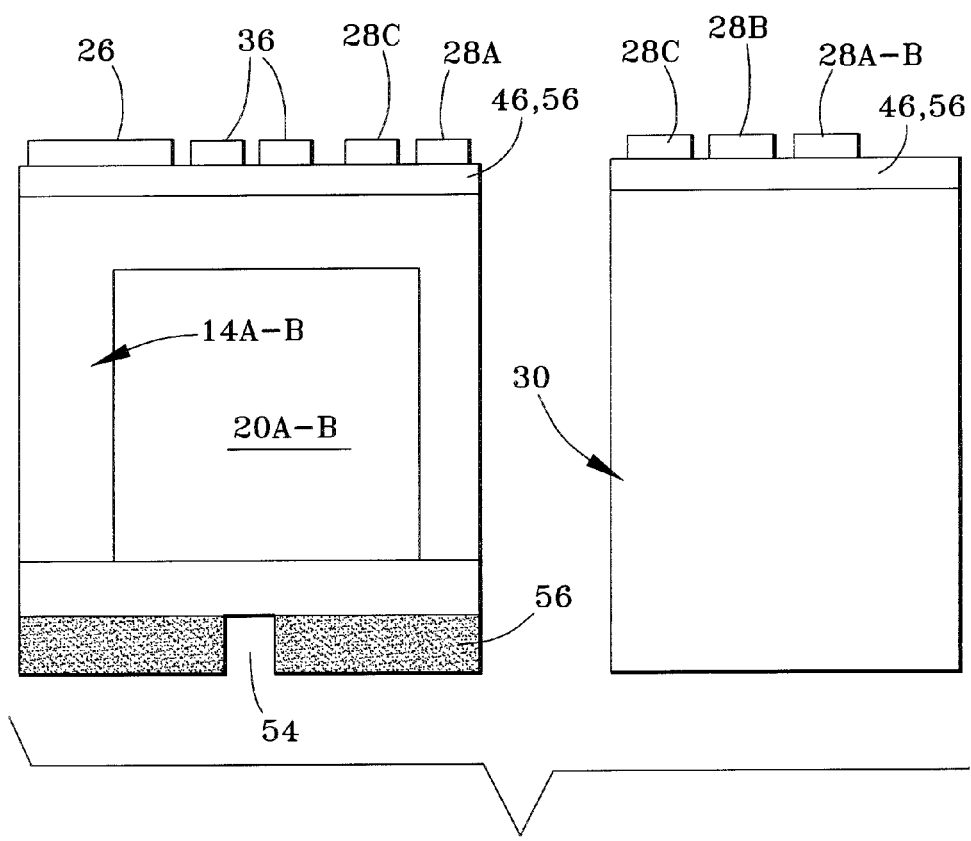
FIG. 9 is a detailed cross-sectional view through a fluid inlet/outlet of one of the tube portions of FIGS. 1 through 8.

Finally, FIG. 9 represents a method for defining the ports 22 in the lower surface of the tube structure 14. For illustrative purposes, only one of the tube portions 14A-B is portrayed in FIG. 9. Prior to defining the tube structure 14, a thermal oxide layer 56 can be grown or a suitable film can be otherwise deposited by chemical vapor deposition, etc., on exposed surfaces of the wafer structure from which the tube structure 14 is fabricated. As evident from FIG. 9 (as well as FIGS. 4 and 7), the oxide layer 56 on the upper surface of the wafer structure can be retained and subsequently used as the dielectric layer 46 to electrically insulate the drive and sensing elements 26 and 28A-C from the tube structure 14. Similar to FIG. 8, FIG. 9 shows the temperature sensing element 36 on the dielectric layer 46 of the tube portion 14A-B to obtain a more accurate temperature reading of the fluid within the tube portion 14A-B.

The internal passage 20A-B and outer walls of the tube portions 14A-B can be fabricated by plasma etching, wet etching, grinding, bead blasting, ultrasonic machining, deep reactive ion etching (DRIE), laser machining and other methods known to those skilled in the art. Prior to definition of the outer walls of the tube structure 14, including any desired thinning of the sidewalls of the tube portions 14A and 14B, the oxide layer 56 covering the lower surface of the wafer structure can be etched to define holes 54, after which metal for the drive and sensing elements 26 and 28 and bond pads 34 can be deposited and patterned. A resist is then applied and the outer walls of the tube structure 14 etched. After stripping the resist, the wafer structure can be flipped over and the ports 22 etched in the lower wall of the tube structure 14 using the oxide layer 56 on the lower surface as a mask to etch the ports 22 in the desired locations in the lower surface of the tube portions 14A and 14B. The remaining oxide layer 56 on the upper and lower surfaces of the tube structure 14 can remain to balance any stresses induced by the oxide layer 56.

FIG. 10 represents any one of the devices 10 of FIGS. 1 through 9 installed in a fluidic system 60 through which a fluid is caused to flow. The fluidic system 60 may be any one of a variety of types, but according to a preferred aspect is a type where accuracy and precision are important, such as chemical concentration applications. As previously noted, nonlimiting examples of such systems include medical treatment systems such as drug mixing equipment, drug infusion monitoring or pumping equipment (including intravenous (IV) units), anesthetic delivery equipment and blood purification equipment (including equipment for assisting in functions normally provided by the kidneys, liver or lungs), energy and fuel systems including fuel delivery systems and fuel cell systems employed in stationary and mobile (e.g., vehicular) power generation applications, chemical mixing systems, chemical processing systems, and consumer goods. As such, the fluidic system 60 may contain a wide variety of fluids, which as used herein encompasses liquids, gases, liquid and gas mixtures, solutions, colloids, and suspensions containing a solid or liquid dispersed phase. Particular examples of fluids include fuels, fuel cell solutions (including mixtures of liquids and/or gases), drugs, anesthetics (including mixtures of liquids and/or gases), blood, dialysate, urine, water, nutrients, gases and gas mixtures (including oxygen, hydrogen, helium, neon, nitrogen, argon, nitrous oxide, methane, butane, natural gas, inlet and exhaust gases of various combustion processes, etc.).

The micromachined devices 10 is schematically represented in FIG. 10 as being installed in the fluidic system 60 to sense the concentration of a component of the fluid. In FIG. 10, the device 10 is shown mounted to a line carrying a fluid mixture that is drawn by a pump 64 from a source 62 and pumped to the intended destination/use 66 of the fluid. Other components, including mixing chambers, additional pumps, etc., can also be incorporated into the system 60, as may be appropriate for the intended purpose of system 60. As a nonlimiting example, the system 60 could be a fuel cell system and the device 10 employed to sense the concentration of a fuel, such as methanol, ethanol, isopropyl alcohol (IPA), formic acid, sulfuric acid, gasoline, or other organic liquid, in a mixture delivered to a fuel cell (66), such as a direct methanol fuel cell (DMFC), proton exchange membrane (PEM) fuel cell (or PEMFC), or reformed fuel cell. As well known in the art, in a fuel cell system it is important to precisely know the concentration of the fuel in the fuel mixture to optimize the efficiency of the system. For example, if a methanol-water mixture is used, the fluid density of the mixture can be used to determine the concentration of methanol in the mixture, thereby providing feedback for the purpose of controlling the mixing ratio or flow rate of the fuel mixture.

The lines carrying the fluid to the device 10 are connected to the inlet and outlet ports 22, respectively, of the device 10. A microprocessor or microcontroller 68, noted above as used by the device 10, is represented as being fabricated on a chip that can be mounted or otherwise appropriately coupled to the device 10 in any known manner. As also previously noted, the microcontroller 68 preferably includes appropriate circuitry for amplifying and processing the input and output signals of the drive and sensing elements 26 and 28A-C. A system controller 70 is represented as receiving output from the device 10 and destination/use 66, and as controlling the pump 64 that delivers the fluid from the source 62 to the device 10. FIG. 10 further depicts a bypass passage 72 that is in fluidic parallel to the micromachined device 10 and through which the bulk of the fluid flows directly from the pump 64 to the destination/use 66, in which case only a portion of the fluid passes through and is analyzed by the device 10.

As previously discussed, the entire device 10 can be fabricated as a disposable unit, in which case the substrate 12 and tube structure 14 are preferably fabricated from plastic materials. As a disposable unit, the device 10 can be removed from the system 60 and replaced by another device 10. Such a capability is especially useful in fluidic systems that are intended for multiple uses but the device 10 is susceptible to becoming contaminated by the fluid, as in the case of medical treatment equipment, including but not limited to drug delivery and anesthetic delivery systems. As a disposable unit, it may be more preferable to incorporate much of the circuitry that might otherwise be included in the microcontroller 68, for example, amplification and signal processing circuitry, into the system controller 70 or another remote location, instead of within the on-chip microcontroller 68, such that a significant portion of the electronics required by the device 10 is not discarded but remains with the more durable components of the fluidic system 60.

The components illustrated in FIG. 10 are for illustration only, and those skilled in the art will appreciate that the device 10 can be used singularly, in combination with additional devices 10 (for example, in parallel or series flow path configurations), and in combination with a variety of other components and sensors to monitor the fluidic system 60. For example, an additional device 10 can be placed in the bypass passage 72.

While the invention has been described in terms of certain embodiments, it is apparent that other forms could be adopted by one skilled in the art. Therefore, the scope of the invention is to be limited only by the following claims.

The invention claimed is:

1. A fluidic system containing a micromachined device for determining at least one property of a fluid flowing in the system, the micromachined device comprising:
   a substrate;
   a base structure on the substrate;
   a tube structure extending from the base structure and spaced apart from a surface of the substrate, the tube structure comprising at least one pair of geometrically parallel tube portions substantially lying in a plane, at least one continuous internal passage defined at least in part within the parallel tube portions, and an inlet and outlet of the internal passage fluidically connected to the base structure, the tube structure being configured for vibrational movement in the plane of the tube structure;

at least one drive element in proximity to the tube structure and operable to induce the vibrational movement of the tube structure in the plane of the tube structure and to induce resonant vibrational movements in the tube portions in the plane of the tube structure; and at least one sensing element in proximity to the tube structure and adapted to sense deflections of each of the tube portions in the plane of the tube structure when the tube structure is vibrated with the at least one drive element;

wherein at least a portion of the fluid in the fluidic system flows through the internal passage of the tube structure and at least one property of the fluid portion is determined with the micromachined device.

2. The fluidic system according to claim 1, wherein the substrate is formed of a material chosen from the group consisting of plastic, metal, glass, and ceramic materials.

3. The fluidic system according to claim 2, wherein the tube structure is formed of a material chosen from the group consisting of silicon, doped silicon and other semiconductor materials, diamond, titanium and other metallic materials, dielectric materials, and glass, plastic and ceramic materials.

4. The fluidic system according to claim 1, wherein the substrate is formed of a plastic material.

5. The fluidic system according to claim 4, wherein the tube structure is formed of a material chosen from the group consisting of silicon, doped silicon and other semiconductor materials, diamond, titanium and other metallic materials, dielectric materials, and glass, plastic and ceramic materials.

6. The fluidic system according to claim 1, wherein the fluidic system is a fuel system and the fluid is a fuel.

7. The fluidic system according to claim 6, wherein the fuel system is installed on a vehicle.

8. The fluidic system according to claim 6, wherein the fluidic system is a fuel cell system and the fluid is a fuel cell solution.

9. The fluidic system according to claim 8, wherein the fuel cell system is installed on a stationary or mobile power generation application.

10. The fluidic system according to claim 1, wherein the fluidic system is a medical treatment system.

11. The fluidic system according to claim 10, wherein the medical treatment system is a drug delivery system and the fluid is a drug.

12. The fluidic system according to claim 10, wherein the medical treatment system is an anesthetic delivery system and the fluid is an anesthetic.

13. The fluidic system according to claim 10, wherein the micromachined device is disposable and the substrate and tube structure are formed of plastic materials.

14. The fluidic system according to claim 13, wherein the medical treatment system is a drug delivery system.

15. The fluidic system according to claim 13, wherein the fluidic system comprises amplification and signal processing circuitry for amplifying and processing input and output signals of the drive and sensing elements, and the amplification and signal processing circuitry are not located on the micromachined device.

16. The fluidic system according to claim 10, wherein the medical treatment system is a blood purification system.

17. The fluidic system according to claim 10, wherein the fluid flowing in the fluidic system is blood, dialysate, urine, water, nutrients or oxygen.

18. The fluidic system according to claim 1, wherein the fluidic system is a chemical processing system.

19. The fluidic system according to claim 1, wherein the at least one property of the fluid is chosen from the group consisting of mass flow rate, density, specific gravity, volumetric flow rate, dose, total volume delivered, temperature, chemical concentration, viscosity, and lubricity of the fluid.

20. The fluidic system according to claim 1, wherein the fluidic system comprises a plurality of the micromachined device according to claim 1, and the plurality of micromachined devices are disposed in parallel flow paths within the fluidic system.

21. The fluidic system according to claim 1, wherein the fluid is chosen from the group consisting of liquids, gases, and liquid and gas mixtures.

22. The fluidic system according to claim 1, wherein the fluid is a gas or gas mixture chosen from the group consisting of oxygen, hydrogen, helium, neon, nitrogen, argon, nitrous oxide, methane, butane, natural gas, and inlet and exhaust gases of a combustion process.

23. The fluidic system according to claim 1, wherein the fluid is chosen from the group consisting of solutions, colloids, and suspensions containing a solid or liquid dispersed phase.

24. The fluidic system according to claim 1, wherein the fluidic system further comprises a bypass passage that is in fluidic parallel to the micromachined device.

25. A method of determining at least one property of a fluid flowing in a fluidic system, the method comprising:

placing in the fluidic system a micromachined device having a tube structure comprising at least one pair of geometrically parallel tube portions substantially lying in a plane and at least one continuous internal passage defined at least in part within the parallel tube portions;

operating at least one drive element to induce vibrational movements in the tube structure as the fluid of the fluidic system flows through the internal passage within the tube structure so that the vibrational motion of the tube structure is parallel to the plane of the tube structure and the tube portions resonate about 180 degrees out of phase with each other;

sensing deflections of each of the tube portions in the plane of the tube structure;

producing outputs corresponding to the sensed deflections; and determining from the outputs the at least one property of the fluid.

26. The method according to claim 25, wherein the substrate is formed of a material chosen from the group consisting of plastic, metal, glass, and ceramic materials.

27. The method according to claim 26, wherein the tube structure is formed of a material chosen from the group consisting of silicon, doped silicon and other semiconductor materials, diamond, titanium and other metallic materials, dielectric materials, and glass, plastic and ceramic materials.

28. The method according to claim 25, wherein the substrate is formed of a plastic material.

29. The method according to claim 28, wherein the tube structure is formed of a material chosen from the group consisting of silicon, doped silicon and other semiconductor materials, diamond, titanium and other metallic materials, dielectric materials, and glass, plastic and ceramic materials.

30. The method according to claim 28, further comprising disposing of the micromachined device after a single use.

31. The method according to claim 25, wherein the fluidic system is a fuel system and the fluid is a fuel.

32. The method according to claim 31, wherein the fuel system is installed on a vehicle.

33. The method according to claim 31, wherein the fluidic system is a fuel cell system and the fluid is a fuel cell solution.

34. The method according to claim 33, wherein the fuel cell system is installed on a vehicle.

35. The method according to claim 25, wherein the fluidic system is a medical treatment system.

36. The method according to claim 25, wherein the medical treatment system is a drug delivery system and the fluid is a drug.

37. The method according to claim 25, wherein the medical treatment system is an anesthetic delivery system and the fluid is an anesthetic.

38. The method according to claim 25, further comprising disposing of the micromachined device after a single use.

39. The method according to claim 25, wherein the fluidic system is a chemical processing system.

40. The method according to claim 25, wherein the at least one property of the fluid is chosen from the group consisting of mass flow rate, density, specific gravity, volumetric flow rate, chemical concentration, viscosity, and lubricity of the fluid.

* * * * *